US012378289B2

(12) United States Patent
Duncan et al.

(10) Patent No.: US 12,378,289 B2
(45) Date of Patent: Aug. 5, 2025

(54) RECOMBINANT ONCOLYTIC VIRUSES FOR TREATMENT OF METASTATIC CANCERS

(71) Applicant: ENTOS PHARMACEUTICALS INC., Edmonton (CA)

(72) Inventors: Roy Duncan, Mineville (CA); Chungen Pan, Guangzhou (CN)

(73) Assignee: ENTOS PHARMACEUTICALS INC., Edmonton (CA)

( * ) Notice: Subject to any disclaimer, the term of this patent is extended or adjusted under 35 U.S.C. 154(b) by 625 days.

(21) Appl. No.: 16/626,019

(22) PCT Filed: Jun. 22, 2018

(86) PCT No.: PCT/CA2018/050766
§ 371 (c)(1),
(2) Date: Dec. 23, 2019

(87) PCT Pub. No.: WO2018/232523
PCT Pub. Date: Dec. 27, 2018

(65) Prior Publication Data
US 2020/0123204 A1    Apr. 23, 2020

(30) Foreign Application Priority Data

Jun. 23, 2017 (CA) .............................. CA 2971832

(51) Int. Cl.
| C07K 14/005 | (2006.01) |
| A61K 35/765 | (2015.01) |
| A61K 35/766 | (2015.01) |
| A61P 35/04 | (2006.01) |
| C12N 7/00 | (2006.01) |

(52) U.S. Cl.
CPC .......... *C07K 14/005* (2013.01); *A61K 35/765* (2013.01); *A61K 35/766* (2013.01); *A61P 35/04* (2018.01); *C12N 7/00* (2013.01); *C07K 2319/03* (2013.01); *C12N 2720/12022* (2013.01); *C12N 2720/12033* (2013.01); *C12N 2760/20221* (2013.01); *C12N 2760/20232* (2013.01)

(58) Field of Classification Search
CPC .............. A61K 35/765; A61K 35/766; A61K 2039/5258; A61K 2039/53; A61K 39/215; A61K 2039/5252; A61K 39/12; A61K 2039/70; A61K 39/145; A61P 35/00; A61P 31/14; A61P 37/04; A61P 35/04; C07K 14/005; C07K 2319/00; C07K 2319/03; C12N 15/86; C12N 2760/16134; C12N 2770/36111; C12N 2720/12032; C12N 2760/20232; C12N 13/00; C12N 2760/16234; C12N 2720/12033; C12N 7/00; B01J 19/10; G16B 20/00
See application file for complete search history.

(56) References Cited

U.S. PATENT DOCUMENTS

| 7,052,832 B2 * | 5/2006 | Coffey | ................... A61P 37/06 436/63 |
| 10,603,351 B2 * | 3/2020 | Bell | ....................... A61P 35/00 |
| 2011/0206640 A1 | 8/2011 | Bell et al. | |

FOREIGN PATENT DOCUMENTS

WO    2010/0250056 A1 *    2/2010    ........... A61K 35/766

OTHER PUBLICATIONS

Brown et al. J Virol. Jan. 2009;83(2):552-61. doi: 10.1128/JVI. 01921-08. Epub Oct. 29, 2008.*
Wong Carmen et al. PLOS ONE, Mar. 17, 2016, pp. 1-18.*
Brown et al. Journal of Virology, 2009, vol. 83, No. 2, pp. 552-561.*
Top et al. PLOS Pathogens 2009, vol. 5, No. 3, pp. 1-14.*
Salsman. J Virol, 2005, 79: 8090-8100.*
Brown et al., The p14 FAST Protein of Reptilian Reovirus Increases Vesicular Stomatitis Virus Neuropathogenesis, J. Virol., 83(2):552-561 (2009).
Hastie et al., Vesicular stomatitis virus as a flexible platform for oncolytic virotherapy aganist cancer, J. General. Virol., 93:2529-45 (2012).
Le Boeuf et al., Reovirus FAST Protein Enhances Vesicular Stomatitis Virus Oncolytic Virotherapy in Primary and Metastatic Tumor Models., Mol. Ther. Oncol., 6:80-9 (2017).
Maroun et al., Designing and building oncolytic viruses, Fut. Virol., 12(4):193-213 (2017).
Salsman et al., A Virus-Encoded Cell-Cell Fusion Machine Dependent on Surrogate Adhesins, PLOS Pathogens, 4(3):1-12 (2018).
International Search Report and Written Opinion of the International Search Authority, PCT/CA2018/050766, mailed Sep. 13, 2018.
Alkayyal et al., Oncolytic Rhabdo Virus MG 1-IL 12 Enhances Anti-tumour Immunity, Ottawa Hospital Research Institute Research Day, pp. 1-94, Nov. 2013.
Da Pan et al., Activation of p53 by chemotherapeutic agents enhances reovirus oncolysis, Plos One. 8:e54006 (2013).
Wong et al., Adenovirus-Mediated Expression of the p14 Fusion-Associated Small Transmembrane Protein Promotes Cancer Cell Fusion and Apoptosis In Vitro but Does Not Provide Therapeutic Efficacy in a Xenograft Mouse Model of Cancer, Plos One. 11:e0151516 (2016).

* cited by examiner

*Primary Examiner* — Bao Q Li
(74) *Attorney, Agent, or Firm* — MARSHALL, GERSTEIN & BORUN LLP

(57) ABSTRACT

Disclosed are recombinant oncolytic viruses that express one or more reovirus fusion-associated small transmembrane FAST) proteins and uses thereof. The oncolytic activity of the recombinant oncolytic viruses expressing FAST proteins can be used to treat primary and metastatic cancers, especially from breast and colon cancers.

5 Claims, 11 Drawing Sheets

RECOMBINANT ONCOLYTIC VIRUSES FOR TREATMENT OF METASTATIC CANCERS

CROSS REFERENCE TO RELATED APPLICATIONS

This application is a U.S. national stage of International Application No. PCT/CA2018/050766, filed Jun. 22, 2018, which claims the benefit of Canadian Patent Application No. 2,971,832 filed on Jun. 23, 2017, the entire contents of each of which are fully incorporated herein by reference.

FIELD OF THE INVENTION

The present invention relates to cancer therapeutics. In particular, the invention relates to the use of recombinant oncolytic viruses for treatment of cancers.

BACKGROUND OF THE INVENTION

Recent studies with oncolytic virus (OV) therapy in the treatment of cancer have yielded positive results, with the first OV being licensed for use in the U.S. and Europe in 2015. This interesting new therapeutic approach to the treatment of cancers relies on the ability of OVs to preferentially infect and kill cancer cells while leaving normal cells alone. The OV can destroy tumours via direct virus-mediated cytotoxicity, by inducing a variety of cytotoxic immune effector mechanisms, and/or by triggering vascular collapse of the tumour. Viruses from nine different families have been shown to have oncolytic activity and progressed to clinical trials, including DNA viruses from families Adenoviridae, Herpesviridae, Parvoviridae and Poxviridae, and RNA viruses from families Paramyxoviridae, Picornaviridae, Reoviridae, Retroviridae and Rhabdoviridae. Despite promising pre-clinical results, improved clinical outcomes from OV therapy remain modest. Furthermore, given the genetic diversity of tumour cells, it remains unlikely that a single OV will ever be developed that would serve as a 'magic bullet' to treat all cancers equally. Hence, there remains an unmet need to develop additional OV platforms with increased clinical efficacy.

The fusion-associated small transmembrane (FAST) proteins are a unique family of membrane fusion proteins encoded by the fusogenic reoviruses, and are the only well-characterized examples of membrane fusion proteins encoded by nonenveloped viruses (Ciechonska and Duncan, Trends in Microbiology 22:715-724, 2014). Currently, the FAST proteins include: p10, p13, p14, p15, p16 and p22 (FIG. 1). At 95 to 198 amino acids in size, the FAST proteins are the smallest known viral membrane fusion proteins. Rather than mediating virus-cell fusion, the FAST proteins are non-structural viral proteins that are expressed on the surfaces of virus-infected or -transfected cells, where they induce cell-cell fusion and the formation of multinucleated syncytia. A purified FAST protein, when reconstituted into liposome membranes, induces liposome-cell and liposome-liposome fusion, indicating the FAST proteins are bona fide membrane fusion proteins (Top et al., EMBO J. 24:2980-2988, 2005). Different FAST proteins display different abilities to fuse cells and induce cytotoxicity (Salsman et al., 2005, J Virol 79: 8090-8100), and they share little to no sequence similarity so are not immunologically cross-reactive.

In contrast to enveloped viral fusion proteins, which are large (generally >500 amino acids) and partition the majority of their mass external to the membrane, FAST proteins are small and have an unusual topology that partitions the majority of the protein to the membrane and cytoplasm, exposing exceptionally small ectodomains of just 20 to 43 residues to the extracellular milieu (Shmulevitz and Duncan, EMBO J 19: 902-912, 2000; Corcoran and Duncan, J. Virol 78(8):4342-51, 2004; Dawe et al., J Virol 79(10): 6216-26, 2005; Racine et al., J Virol 83: 5951-5955; Thalmann et al., Virology 402: 26-40, 2010; Guo et al., Virus Res 171: 129-137, 2013). Functional studies reveal the FAST proteins are modular fusogens, with the ectodomain, transmembrane (TM) domain and cytoplasmic endodomain all exerting an active role on the membrane fusion process (Barry and Duncan, J Virol 83: 12185-12195; Clancy and Duncan, J Virol 83: 2941-2950; Key and Duncan, PLOS Pathogens 10: e1004023). While there is little to no conserved amino acid identity between different FAST proteins, their fusion modules are functionally interchangeable, although not all combinations are tolerated (Clancy and Duncan, J Virol 83: 2941-2950; Clancy and Duncan, J Virol 85: 4707-4719, 2011).

Despite the diminutive size of their ectodomains, several FAST proteins have been shown to contain small, amphiphilic, structurally dynamic ectodomain motifs that induce lipid mixing (FIG. 1). These motifs resemble the fusion peptides (FPs) encoded by enveloped viral fusion proteins (Corcoran et al., J Biol Chem 279(49): 51386-94, 2004; Shmulevitz et al., J Virol 78(6):2808-18, 2004; Top et al., J Biol Chem 287: 3403-3414, 2012; Barry et al., J Biol Chem 285: 16424-16433, 2010; Key et al., BBA Biomembranes 1848: 408-416, 2015), although with unique structural features. The p14 FP comprises the N-terminal 21 residues of the protein, and requires an N-terminal myristate moiety to mediate lipid mixing. Nuclear magnetic resonance (NMR) spectroscopy revealed two proline residues within the p14 FP form a protruding loop structure presenting valine and phenylalanine residues at the apex and connected to the rest of the protein by a flexible linker region (Corcoran et al., J Biol Chem 279(49): 51386-94, 2004). The 40-residue p10 ectodomain contains a 25-residue N-terminal FP with two conserved cysteine residues that form an intramolecular disulfide bond, generating an 11-residue cystine noose required to force solvent exposure of hydrophobic residues and induce lipid mixing (Shmulevitz et al., J Virol 78(6): 2808-18, 2004; Barry et al., J Biol Chem 285: 16424-16433, 2010; Key et al., BBA Biomembranes 1848: 408-416, 2015). The p10 FP somewhat resembles the internal fusion peptides of the Ebola virus and avian leukosis and sarcoma virus (ALSV) glycoproteins (Delos et al., J Virol 74(4): 1686-93, 2000; Delos and White, J Virol 74(20):9738-41, 2000; Gallaher, 1996; Ito et al., J Virol 73(10):8907-12, 1999; Ruiz-Arguello et al., J Virol 72(3): 1775-81, 1998), although the cystine noose structure is a unique feature of the p10 FP. The p10 FP is connected through a two-residue linker to a 13-residue membrane-proximal ectodomain region (MPER), which constitutes a second, independent motif governing reversible, cholesterol-dependent assembly of p10 multimers into plasma membrane fusion platforms (Key and Duncan, PLOS Pathogens 10: e1004023). The 20-residue, myristoylated ectodomain of the p15 FAST protein comprises a FP with a 6-residue polyproline helix flanked by small, unstructured N- and C-termini; both the polyproline helix and myristate are required for fusion activity (Top et al., J Biol Chem 287: 3403-3414, 2012).

The FAST protein TM domain functions as a reverse signal-anchor motif (Wahlberg and Spiess, J Cell Biol 137: 555-562), directing and anchoring the FAST protein in the membrane in a bitopic N-out/C-in topology (FIG. 1). FAST protein TM domains can be functionally interchanged between the different FAST proteins, but they cannot be functionally replaced by TM domains from enveloped virus fusion proteins or cellular proteins (Clancy and Duncan, J Virol 83: 2941-2950), indicating there are family-specific features of a FAST protein TM domain required for fusion activity.

The FAST protein endodomains contain several motifs required for function (FIG. 1). The membrane-distal p10 and p14 cytoplasmic tails are required for fusion activity, but are intrinsically disordered and can be replaced by a scrambled sequence and maintain function (Barry and Duncan, J Virol 83: 12185-12195). All FAST protein endodomains contain a membrane-proximal polybasic (PB) motif, which in the case of p14 interacts with activated Rab11 to sort p14 into AP1 vesicles for Golgi export to the plasma membrane (Parmar et al., Mol Biol Cell 25: 866-878, 2014). The p14 and p15 FAST proteins contain an amphipathic helix or helix-kink-helix motif adjacent to the PB motif, which function as fusion-inducing lipid packing sensors (FLiPS) to promote pore formation (Read et al., PLOS Pathogens 11: e1004962, 2015). The p10 FAST protein lacks the FLiPS motif but has a unique palmitoylated di-cysteine motif adjacent to the cytoplasmic side of the membrane that may serve a similar function (Shmulevitz et al., J Virol 77:9769-9779).

Prior art reveals that enveloped virus membrane fusion protein that fuse membranes at physiological pH, such as the membrane fusion protein of gibbon ape leukaemia virus (GALV), can enhance the efficacy of OVs based on the undefined mechanism by which the fusion protein contributes to tumor destruction (Nakamori et al., 2004, Mol Ther. 9: 658). Unlike enveloped virus fusion proteins, FAST proteins evolved specifically to induce cell-cell, not virus-cell, fusion. This distinct evolutionary imperative is reflected in their distinct structural features, described above. Functional comparisons also indicate the distinct structural properties of enveloped virus fusion proteins and FAST proteins are reflected in different mechanisms of membrane fusion (Clancy et al., Virology 397: 119-129, 2010), suggesting FAST proteins likely differ from enveloped virus fusion proteins in their mechanism of cell destruction. FAST proteins are also considerably smaller than enveloped virus fusion proteins, removing size constraints that can limit the use of enveloped virus fusion proteins.

Specific targeting of cancer cells is essential for oncolytic virotherapy and can be achieved in several ways. Some virus such as H1 autonomously replicating parvoviruses, reovirus, Newcastle Disease Virus, Mumps virus, Moloney leukemia virus have a natural preference for cancer cells, whereas viruses such as measles, adenovirus, Vesicular Stomatitis Virus, vaccinia and Herpes Simplex Virus can be adapted or engineered to make them cancer-specific (Russell S J et al., Nat Biotechnol 30(97): 658-670, 2012). In addition, improving the ability of the OV to cause destruction of the tumor cells and induce anti-tumor immune responses are important considerations in developing OVs.

SUMMARY OF THE INVENTION

According to an aspect of the present invention, there is provided a recombinant oncolytic virus that expresses one or more reovirus fusion-associated small transmembrane (FAST) proteins.

According to another aspect of the present invention, there is provided a recombinant oncolytic virus gene construct comprising a reovirus fusion-associated small transmembrane (FAST) protein gene.

In one embodiment, the FAST protein is p10 derived from avian reoviruses or bat reoviruses; p13 protein derived from bat reoviruses; p14 protein derived from reptilian reoviruses; p15 protein derived from baboon reoviruses; p16 protein derived from an aquareoviruses; p22 protein derived from an aquareoviruses, or combinations thereof. Preferably, the FAST protein is p14, p15 or a combination of domains from p14 and p15.

In another embodiment, the oncolytic virus is derived from herpesvirus, adenovirus, reovirus, measles virus, Newcastle disease virus, vaccina virus and vesicular stomatitis virus. Preferably, the oncolytic virus is vesicular stomatitis virus.

According to a further aspect of the present invention, there is provided a method for treating cancer comprising administering the recombinant oncolytic virus of described above to a subject in need thereof.

According to yet a further aspect of the present invention, there is provided use of the recombinant oncolytic virus as described above for treatment of cancer.

In one embodiment, the cancer is a breast or colon cancer.

In another embodiment, the cancer is a metastatic cancer.

In one embodiment, the FAST protein is p10 derived from avian reoviruses or bat reoviruses; p13 protein derived from bat reoviruses; p14 protein derived from reptilian reoviruses; p15 protein derived from baboon reoviruses; p16 protein derived from an aquareoviruses; p22 protein derived from an aquareoviruses, or combinations thereof. Preferably, the FAST protein is p14, p15 or a combination of domains from p14 and p15.

In another embodiment, the oncolytic virus is derived from herpesvirus, adenovirus, reovirus, measles virus, Newcastle disease virus, vaccina virus and vesicular stomatitis virus. Preferably, the oncolytic virus is vesicular stomatitis virus.

According to a still further aspect of the present invention, there is provided a recombinant oncolytic virus that expresses one or more non-enveloped viral membrane fusion protein. The one or more non-enveloped viral membrane fusion protein comprising: a transmembrane (TM) domain; a cytosolic, membrane-proximal cluster of three or more basic amino acids; an at least one post-translational fatty acid modification, and an N-terminal ectodomain.

In one embodiment, the one or more non-enveloped viral membrane fusion protein primary sequence is 200 amino acids or fewer.

In another embodiment, the one or more non-enveloped viral membrane fusion protein, when expressed, induces cell-cell fusion and/or syncytium.

In one embodiment, the FAST protein is p10 derived from avian reoviruses or bat reoviruses; p13 protein derived from bat reoviruses; p14 protein derived from reptilian reoviruses; p15 protein derived from baboon reoviruses; p16 protein derived from an aquareoviruses; p22 protein derived from an aquareoviruses, or combinations thereof. Preferably, the FAST protein is p14, p15 or a combination of domains from p14 and p15.

In another embodiment, the oncolytic virus is derived from herpesvirus, adenovirus, reovirus, measles virus, Newcastle disease virus, vaccina virus and vesicular stomatitis virus. Preferably, the oncolytic virus is vesicular stomatitis virus.

In a further embodiment, the vesicular stomatitis virus comprises a deletion at position 51 in a matrix protein.

In a still further embodiment, the one or more non-enveloped viral membrane fusion protein is a chimeric protein.

BRIEF DESCRIPTION OF THE DRAWINGS

These and other features, aspects and advantages of the present invention will become better understood with regard to the following description and accompanying drawings wherein.

DESCRIPTION OF THE INVENTION

The following description is of an illustrative embodiment by way of example only and without limitation to the combination of features necessary for carrying the invention into effect.

Figure 1:
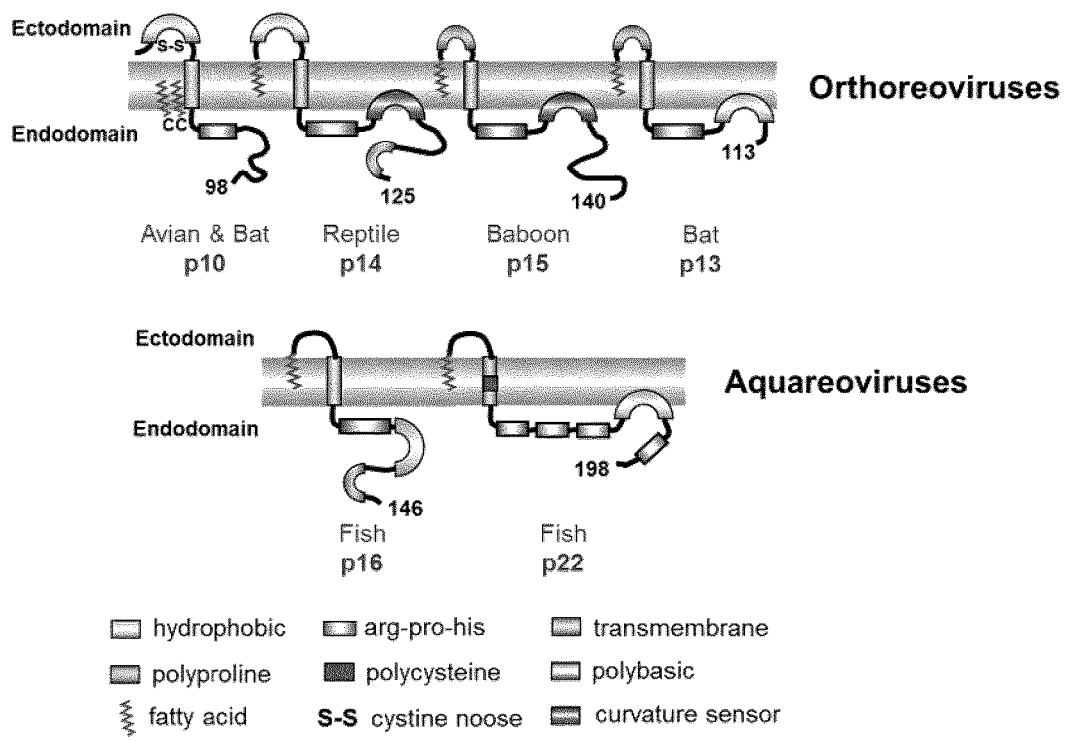
FIG. 1 represents the membrane topology and repertoire and arrangement of structural motifs in the known fusion-associated small transmembrane (FAST) proteins. NOTE: avian and bat reoviruses encode homologous p10 proteins (p10/ARV and p10/NBV, respectively) with the same repertoire and arrangement of structural motifs, but they share only ~30% amino acid identity.
Figure 2:
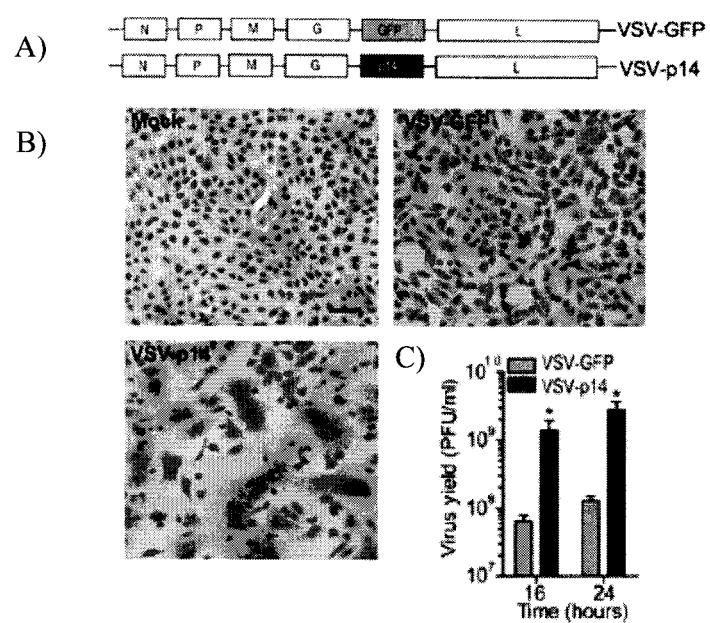
FIG. 2 represents recombinant oncolytic vesicular stomatitis virus (VSV) constructs encoding GFP (VSV-GFP) or the p14 FAST protein (VSV-p14) and their effects on cell-cell fusion and virus replication. (A) Schematic of recombinant VSV containing gene insertions encoding either GFP or the p14 FAST protein. (B) Vero cells were mock-infected or infected with the indicated recombinant viruses at a MOI=0.1 and Giemsa-stained at 24 hpi to detect syncytium formation. (C) As in panel B, using the supernatant from infected cultures to determine the virus yield by plaque assay at the indicated times post-infection. Results are mean±SEM from duplicate experiments (*$p<0.05$ compared to VSV-GFP)
Figure 3:
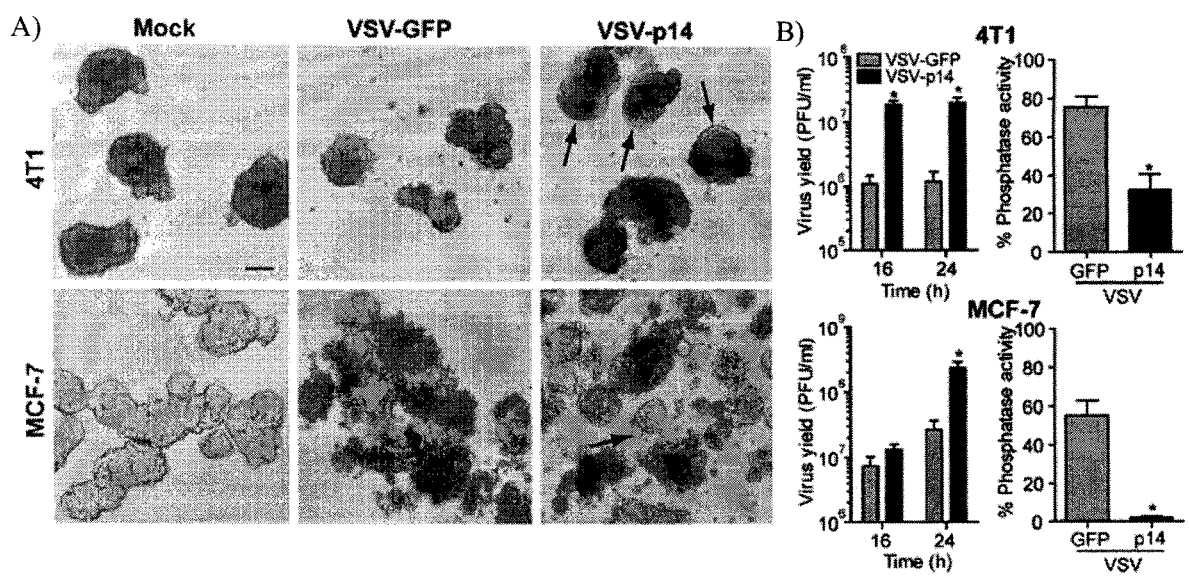
FIG. 3 represents the effects of VSV-GFP and VSV-p14 on breast cancer spheroid cell death and virus yields. (A) 4T1 and MCF-7 breast cancer cells growing as spheroids were mock-infected or infected with $1 \times 10^5$ PFU/ml of recombinant VSV-GFP or VSV-p14, and phase-contrast images of the infected spheroids were captured at 24 hpi. (B) As in panel A, quantifying virus yields in the supernatants at the indicated times post-infection by $TCID_{50}$ in permissive Vero cells (left panels), or quantifying cell viability at 40 hpi using a phosphatase assay (right panels). Phosphatase assay results are reported as mean±SEM percent cell viability from duplicate (MCF-7) or triplicate (4T1) experiments relative to mock-infected spheroid cultures (*$p<0.05$ compared to VSV-GFP)
Figure 4:
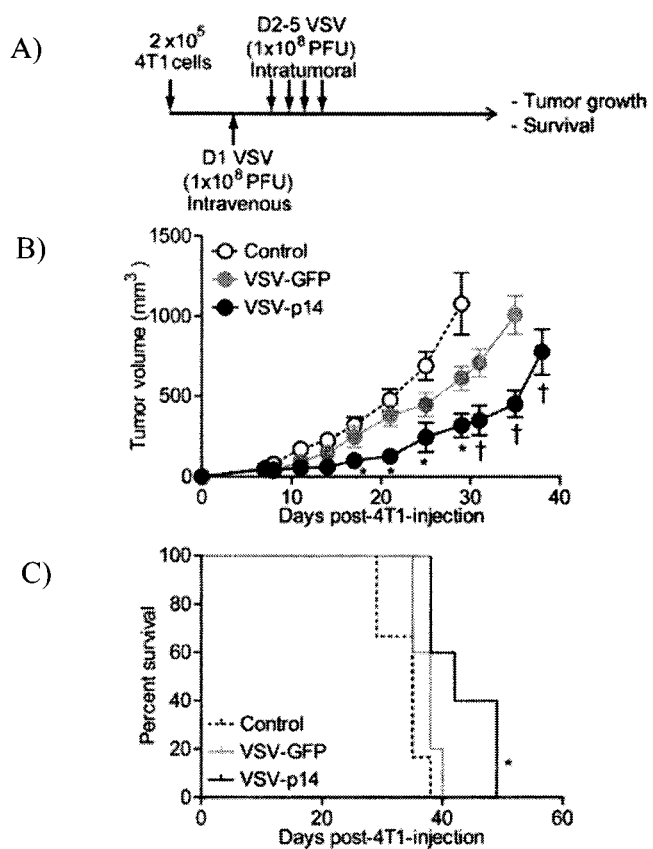
FIG. 4 represents the effects of VSV-GFP and VSV-p14 on the growth of primary mammary tumors and animal survival. (A) Syngeneic 4T1 subcutaneous mammary tumors were established in BALB/c mice and ten days later animals were mock-treated or treated by one intravenous injection of VSV-GFP or VSV-p14 ($1 \times 10^8$ pfu) followed by four intratumoral injections at the same virus dose (N=5 per treatment group). (B) Tumor size was monitored over time and average tumor volumes±SEM were calculated for each treatment group. Statistical analysis used ANOVA to compare VSV-p14 to VSV-GFP (*$p<0.05$ compared to control; †$p<0.05$ compared to VSV-GFP). (C) Survival advantage was assessed by the log-rank (Mantel-Cox) (*$p<0.05$ compared to control)
Figure 5:
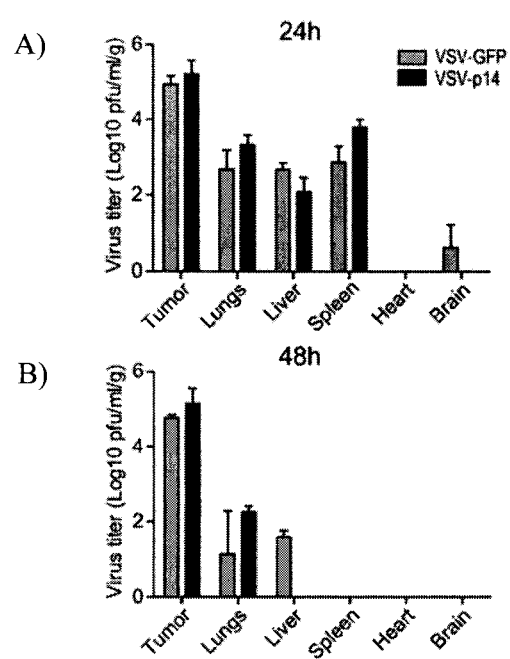
FIG. 5 represents the biodistribution of VSV-GFP and VSV-p14 in animals bearing primary mammary tumors. Subcutaneous 4T1 mammary tumors were established in BALB/c mice, and then animals were treated with one intravenous injection ($1 \times 10^8$ pfu) of VSV-p14 or VSV-GFP. Mice were sacrificed at (A) 24 hpi (N=3 per treatment group) or (B) 48 hpi (N=2 per treatment group), tumors and the indicated organs were harvested, and virus titers were quantified by plaque assay. Results are the average titer per gm of tissue±SEM.
Figure 6:
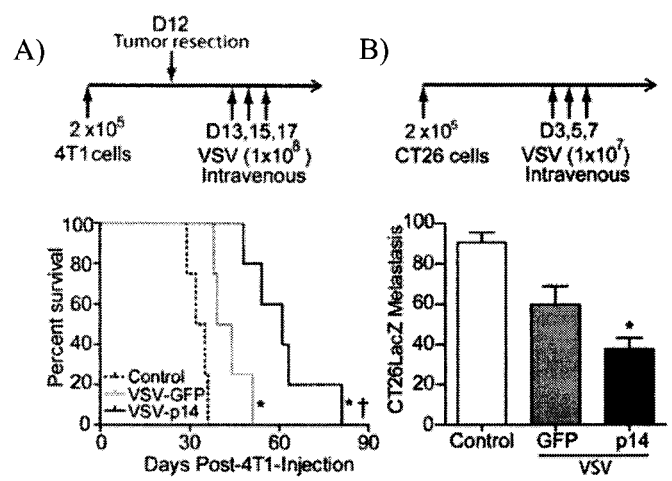
FIG. 6 represents the effects of VSV-GFP and VSV-p14 on animal survival and lung metastases in metastatic models of breast cancer and colon cancer. (A) Subcutaneous 4T1 mammary tumors were established in BALB/c mice and primary tumors were resected on day 12. Mice were treated on days 13, 15 and 17 with PBS, VSV-GFP or VSV-p14 (N=5 per group). Survival advantage was assessed by the log-rank (Mantel-Cox) (*$p<0.016$ compared to PBS, †$p<0.016$ compared to VSV-GFP). (B) CT26LacZ colon carcinoma cells ($2 \times 10^5$ cells) were injected intravenously into BALB/c mice to establish lung metastases. Animals were injected intravenously with PBS (Control, N=8) or with $1 \times 10^7$ pfu of VSV-p14 (N=8) or VSV-GFP (N=7) on days 3, 5 and 7, and lungs were removed 7 days following the last virus injection and the mean±SEM number of surface lung metastases were visually quantified following staining of the excised lungs for (β-galactosidase (*$p<0.05$ compared to control)
Figure 7:
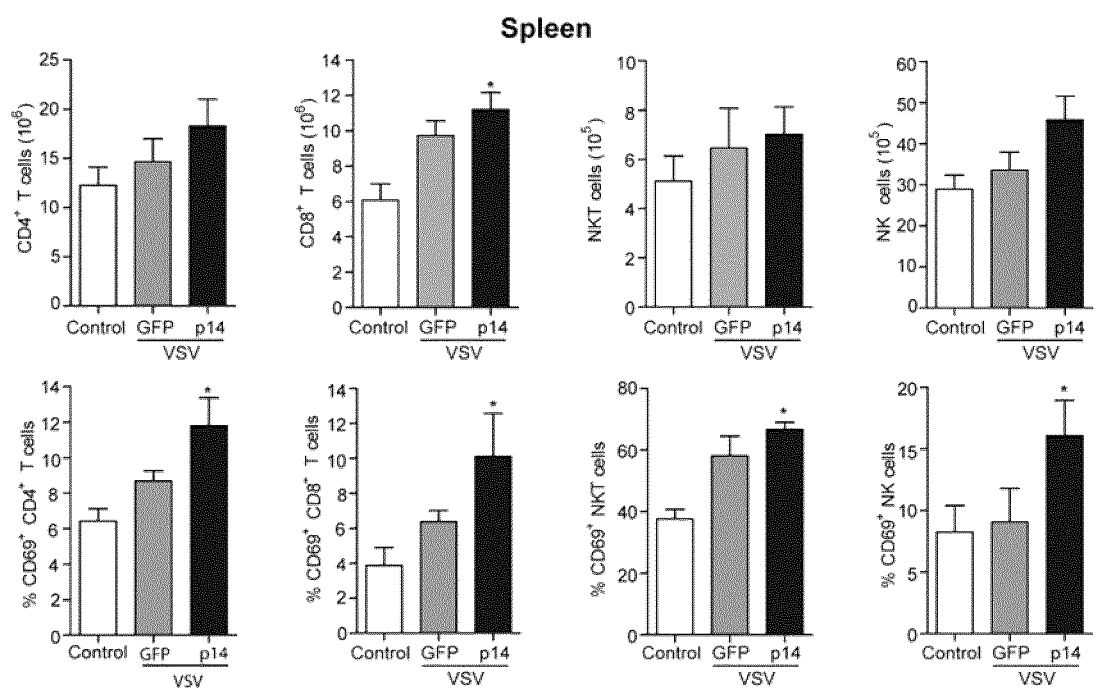
FIG. 7 represents the effects of VSV-GFP and VSV-p14 on activation of splenic T cells and NK cells in a primary breast cancer model. 4T1 tumor-bearing mice (N=9-10 per treatment group) received one intravenous injection of PBS (Control) or VSV-p14 or VSV-GFP ($1 \times 10^8$ pfu) on day 12, followed by similar intratumoral inoculations on days 13, 14 and 15. Spleen cells were isolated 24 h following the final injection. The number of splenic CD4 T cells (CD4$^+$ TcRβ$^+$), CD8 T cells (CD8$^+$ TcRβ$^+$), NKT cells (CD1d-tetramer$^+$ TcRβ$^+$) and NK cells (CD49b$^+$ TcRβ$^-$) (top row), and expression of CD69 by CD4 T cells, CD8 T cells, NKT cells and NK cells (bottom row) was assessed by flow cytometry (*$p<0.05$ compared to control)
Figure 8:
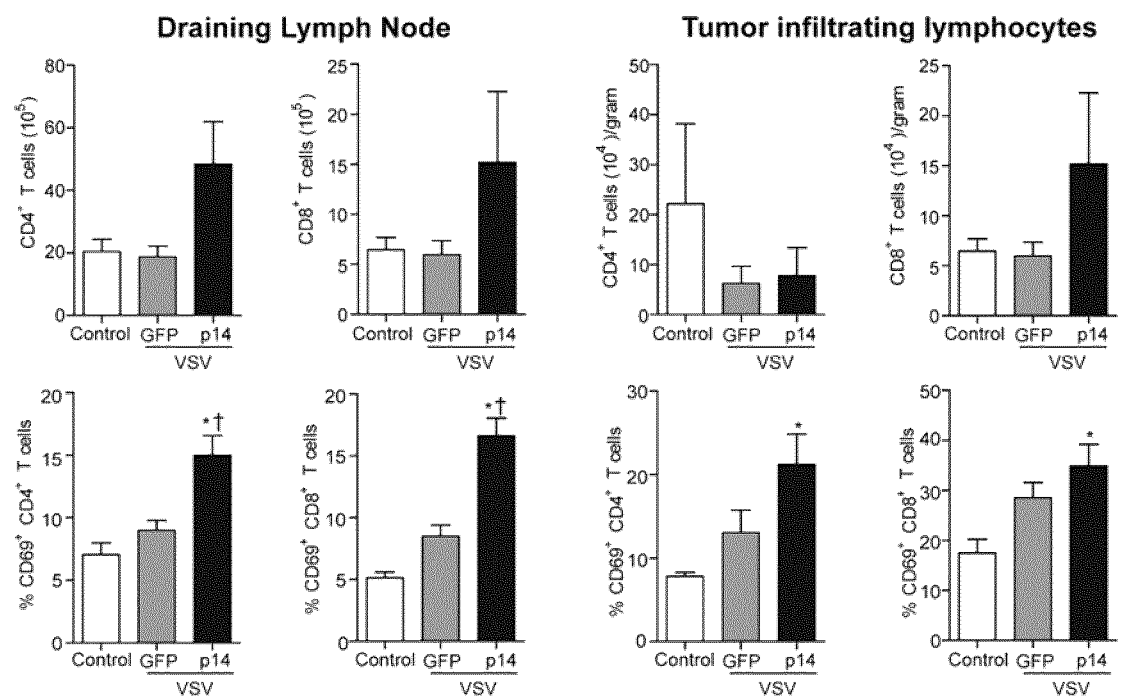
FIG. 8 represents the effects of VSV-GFP and VSV-p14 on the frequency of activated T cells in the tumors and draining lymph node in a primary breast cancer model. 4T1 tumor-bearing mice (N=9-10 per treatment group) received one intravenous injection of PBS (Control) or VSV-p14 or VSV-GFP ($1 \times 10^8$ pfu) on day 12, followed by similar intratumoral inoculations on days 13, 14 and 15. The draining lymph node and tumors were isolated 24 h following the final injection. The number of CD4 T cells (CD4$^+$ TcRβ$^+$) and CD8 T cells (CD8$^+$ TcRβ$^+$) in the draining lymph node and tumors (top row), or the frequency of the same cells expressing the early activation marker CD69$^+$ was assessed using flow cytometry (*$p<0.05$ compared to control; †$p<0.016$ compared to VSV-GFP)

The recombinant oncolytic virus described herein expresses one or more reovirus fusion-associated transmembrane (FAST) proteins. The FAST proteins increase cell-cell fusion which enhances cell-cell virus transmission, and they are cytotoxic and induce a pro-inflammatory response (FIGS. 7 and 8).

By "polypeptide" or "protein" is meant any chain of amino acids, regardless of length or post-translational modification (e.g. glycosylation or phosphorylation). Both terms are used interchangeably in the present application.

FAST proteins are the smallest known membrane fusion proteins, rendering them weakly immunogenic, and their small size facilitates incorporation of FAST protein genes into almost any OV platform, alone or in combination with other immunostimulatory genes. FAST proteins are also not reliant on specific cell receptors and thus fuse numerous cell types, humans have no pre-existing immunity against FAST proteins (they derive from non-human viruses), they promote localized and disseminated virus transmission via syncytium formation at physiological pH, and they are cytocidal and disrupt calcium homeostasis, two mechanisms likely to increase immunogenic cell death and trigger anti-tumor immune responses. Here it is shown that addition of p14 to VSV increases cancer cell death and virus transmission within tumors, reduces tumor growth and metastases, stimulates more robust innate and adaptive immune responses, and improves outcomes in primary and metastatic models of cancer, all while maintaining a favorable safety profile. The FAST proteins therefore provide a novel approach to enhance oncolytic virotherapy by increasing cytocidal and immune-mediated tumor cell killing.

In one aspect of the invention, FAST proteins are provided which are encoded by the genome of viruses in the Reoviridae. FAST proteins are an evolutionarily related family of viral membrane fusion proteins (Nibert and Duncan, PLOS One 8:e68607, 2013), and the only family of nonenveloped virus membrane fusion proteins. Defining features of all family members are: (1) small size (<200 amino acids); (2) a single transmembrane (TM) domain that functions as a reverse signal-anchor to direct a bitopic, N-out/C-in membrane topology; (3) a cytosolic, membrane-proximal cluster of three or more basic amino acids; (4) a post-translational fatty acid modification involving either a myristoylated N-terminus or one or more palmitoylated cysteine residues; (5) a small (<50 residues), N-terminal ectodomain containing a membrane destabilizing motif sharing features of fusion peptides (FPs). Additional features present in some, but possibly not all, FAST proteins include: (1) a cytosolic, membrane-proximal amphipathic helix motif; (2) an intrinsically disordered C-terminal tail.

The family Reoviridae includes the genus *Orthoreovirus*, which includes avian, mammalian and reptilian reoviruses, as well as the genus *Aquareovirus*. For example, the FAST proteins are one or more of p10 proteins derived from species Avian reovirus (ARV) or bat reoviruses in the species Nelson Bay orthoreovirus (NBV); p13 protein derived from a bat reovirus in the proposed new species Broome orthoreovirus (BroV); p14 protein derived from isolates in the species Reptilian orthoreovirus (RRV); p15 protein derived from isolates in the species Baboon orthoreovirus; p16 protein derived from isolates in the species Aquareovirus-C or Aquareovirus-G; p22 protein derived from isolates in the species Aquareovirus-A, and combinations thereof, such as the p14/p15 fusion described in US Patent Publication No. 2014/0314831 (the contents of which is incorporated in its entirety herein). In some cases, a single type of FAST protein may be expressed, such as, but not limited to, p14 or p15, whereas, in other cases, a hybrid oncolytic virus may be produced that expresses a recombinant of more than one type of FAST protein, such as, but not limited to, a combination of different domains from p14 and p15.

Oncolytic viruses (OVs) are naturally occurring or genetically engineered viruses that preferentially replicate within and kill cancer cells due to signaling defects in cellular metabolism and innate immunity (Bell and McFadden, Cell Host Microbe 15: 260-265, 2014). A number of viruses can be used for this purpose, including, but not limited to, herpesvirus, adenovirus, reovirus, measles virus, Newcastle disease virus, vaccina virus and vesicular stomatitis virus.

In one embodiment, the recombinant oncolytic virus is vesicular stomatitis virus (VSV) and the FAST protein is p14, p15 or a recombinant peptide thereof. Preferably, the VSV contains a mutation in the matrix (M) gene that renders the virus highly-susceptible to interferon (IFN) responses (VSVΔ51)

As used herein, the terms "pharmaceutically acceptable", "physiologically tolerable" and grammatical variations thereof, as they refer to compositions, carriers, diluents, and reagents, are used interchangeably and represent that the materials are capable of administration to a mammal without the production of undesirable physiological effects such as nausea, dizziness, gastric upset, and the like.

Methods for the preparation of a pharmacological composition that contains active ingredients, such as the recombinant oncolytic virus described herein, dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol, or the like, as well as combinations thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Physiologically tolerable carriers are well known in the art. Exemplary liquid carriers are sterile aqueous solutions that contain no materials other than the active ingredients and water, or contain a buffer such as sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol, and other solutes.

Liquid compositions can also contain liquid phases in addition to and to the exclusion of water. Exemplary of such additional liquid phases are glycerin, vegetable oils such as cottonseed oil, and water-oil emulsions.

A therapeutically effective amount is a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. In some instances, it may be particularly advantageous to administer such compounds in depot or long-lasting form. A therapeutically effective amount is typically an amount of a fusion protein according to the invention, or polypeptide fragment thereof that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml.

Unless otherwise specified, all references cited are incorporated herein.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein set forth, and as follows in the scope of the appended claims.

EXAMPLES

Cells: African green monkey (Vero) cells were maintained in Dulbecco's Modified Eagle Medium (DMEM) supplemented with 5% Fetal Bovine Serum (FBS). QM5 (Quail muscle fibrosarcoma) cells were cultured in Medium 199 supplemented with 10% FBS. Mouse mammary epithelial (4T1) tumor cells were maintained in complete Roswell Park Memorial Institutes Media (RPMI-1640) supplemented with 10% FBS. MCF-7 cells were cultured in Dulbecco's Modified Eagle Medium/Nutrient Mixture F-12 (DMEM/F-12) supplemented with 10% FBS. Mouse colon carcinoma (CT26LacZ) cells were cultured in DMEM with 10% FBS. All culture reagents were obtained from Gibco, and all cells were cultured as monolayers at 37° C. with 5% CO2.

Mice: Female BALB/c mice were purchased form Charles River Laboratories (Senneville, Canada) and used at 8-12 weeks of age. All animal protocols followed the guidelines of the Canadian Council on Animal Care, and were approved by the University Committee on Laboratory Animals.

Generation of recombinant VSV: The p14 FAST protein gene in pcDNA3 and the EGFP gene in pEGFP-N1 were amplified by PCR and subcloned into the XhoI and NheI sites located between the G and L genes in pVSVΔ51-XN to generate pVSVΔ51-XN-p14 and pVSVΔ51-XN-GFP (hereinafter referred to as VSV-p14 and VSV-GFP). QM5 cells were infected with the modified vaccinia virus Ankara strain expressing T7 RNA polymerase (MVA-T7), and 4 hours later co-transfected with four plasmids at a ratio of 2:2:1.25:0.25 µg: pVSVΔ51-XN-p14 or pVSVΔ51-XN-GFP, and pBS-N, pBS-P and pBS-L, encoding the VSV N, P and L proteins, respectively, under the control of a CMV promoter. Two days later, cell culture supernatants were harvested, filtered through a 0.2 µm filter to remove vaccinia virus, and then used to infect Vero cells. Vero cell supernatants were harvested 3 days post-infection, and the recombinant VSV particles were isolated by plaque purification on Vero cells. The identities of the recombinant viruses were confirmed by sequencing cDNA amplicons obtained by PCR using primers complementary to VSV sequences flanking the insertion site. Virus stocks were amplified and titered by plaque assay using Vero cells. Similar approaches were used to clone the genes encoding the p10/ARV, p10/NBV and p15 FAST proteins into the same pVSVΔ51-XN plasmid and to generate and isolate recombinant VSVΔ51 encoding these FAST proteins.

Oncolytic activity in cell culture: Recombinant viruses were tested for their cytolytic activity in cell culture using Vero cells, 4T1 breast cancer cells, and breast cancer spheroids. Vero cells cultured in 12-well plates were infected with recombinant viruses at a multiplicity of infection (MOI) of 0.1 for 1 hr at 37° C., then cells were washed with PBS to remove unbound virus. Cells were then cultured in fresh medium for 24 hrs. Culture supernatants were harvested to quantify virus yield by plaque assay, and monolayers were stained with Wright-Giemsa to view cell death and syncytium formation under bright-field microscopy. To obtain spheroid cultures, MCF-7 and 4T1 breast cancer cells were seeded into ultra-low attachment Costar 6-well plates using $3 \times 10^4$ cells/well and cultured in a mammosphere medium (DMEM/F-12 supplemented with 20 ng/mL bFGF, 20 ng/mL EGF, 100 U/mL penicillin, 100 µg/mL streptomycin and 1×B27 serum-free supplement), and cultured for 7-9 days, replacing the medium with fresh medium every 72 hrs. Spheroid cultures were infected using $1 \times 10^5$ PFU/well of VSV-GFP or VSV-p14, culture supernatants were harvested at 16-24 hrs post-infection (hpi), and virus yields were determined by $TCID_{50}$ in permissive Vero cells. Cell viability was assessed by incubating resuspended spheroids in PBS at a 1:1 ratio (final volume 1 ml) with phosphatase solution (0.1M sodium acetate, pH 5.5, 0.1% Triton X-100, 4 mg/ml phosphatase substrate) for 90 min at 37° C. in the dark. After incubation, 50 µM of 1 N NaOH was added to each sample to stop the reaction, samples were cleared by centrifugation at 1000×g for 5 min, and supernatants were transferred to 96-well plates to measure absorbance at 405 nm using an Asys Expert 96 Microplate Reader Immunocompetent animal tumor models: Primary breast cancer model: 4T1 breast cancer cells were harvested in the logarithmic growth phase, resuspended in saline, and injected subcutaneously ($2 \times 10^5$ cells in 50 µl) into the mammary fat pad of female BALB/c mice (n=5/treatment group). Palpable tumors formed within 10 d after seeding. Mice were injected intravenously with VSV-GFP or VSV-p14 ($1\times10^8$ PFU/mouse in 50 µl), followed by four similar intratumoral injections one day apart. For the efficacy studies, 4T1 tumors were measured every 2-4 d using an electronic caliper, and tumor volume was calculated as (W×W×L)/2. For biodistribution studies, BALB/c mice with established 4T1 subcutaneous breast tumors were injected intravenously with VSV-GFP or VSV-p14 ($1\times10^8$ pfu/mouse in 50 µl), mice were sacrificed 24-48 hpi, and normal organs (lungs, liver, spleen, heart, brain) and tumor tissues were harvested for virus titration by plaque assay, as previously described.

Figure 9:
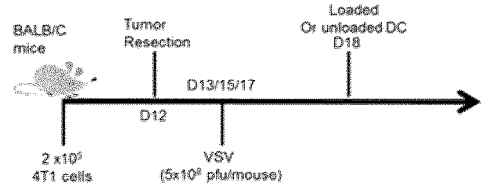
FIG. 9 represents the effects of VSV-GFP and VSV-p14 in combination with adoptive immune cell transfer on survival of animals bearing metastatic mammary tumors. Subcutaneous 4T1 mammary tumors were established in BALB/c mice and primary tumors were resected on day 12. Mice were treated on days 13, 15 and 17 with PBS, VSV-GFP or VSV-p14 (N=5 per group) and on day 18 with adoptive immune cell transfer using dendritic cells loaded with α-galactosylceramide to activate NKT cells, and survival advantage was assessed by the Kaplan-Meier estimator.
Figure 9:
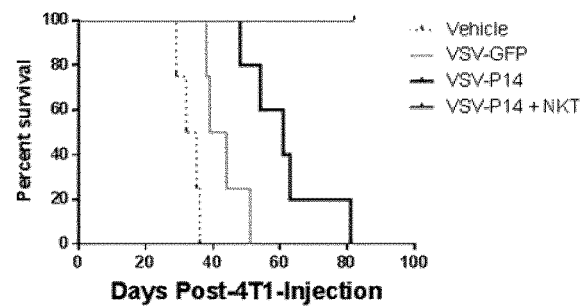

Post-surgical breast cancer metastasis model: 4T1 tumors were established in mice, as described above, and primary tumors were resected 12 days following tumor inoculation, as previously described. On days 13, 15 and 17 mice received 100 µl intravenous injections of PBS or $1\times10^8$ plaque forming units (PFU) of VSV-GFP or VSV-p14. Survival was monitored over time (FIG. 9).

Lung metastasis model: CT26-LacZ colon carcinoma cells ($2\times10^5$ in 50 µl) were injected intravenously into BALB/c mice, and at days 3, 5 and 7 mice were injected intravenously with VSV-GFP or VSV-p14 ($1\times10^8$ PFU/mouse) or with PBS. Mice were sacrificed 7 days following the last virus injection, lungs were harvested, and lung metastases were quantified visually following staining of the tumors using X-gal (Sigma-Aldrich).

Immune phenotyping: BALB/c mice were inoculated with $2\times10^5$ 4T1 cells in the fourth mammary fat pad. Twelve days after inoculation, mice received intravenous injections of PBS, VSV-GFP or VSV-p14. On days 13, 14, 15 mice received intratumoral injections of PBS, VSV-GFP or VSV-p14. Spleens, draining lymph nodes and primary tumors were isolated on day 16. Following mechanical dispersion, tumor infiltrating lymphocytes were enriched by centrifugation through a 33% Percoll gradient (GE Healthcare; Baie d'Urfe, Canada). Red blood cells were lysed with ammonium chloride buffer and cells were washed by centrifugation. The immune profile of lymphoid and myeloid populations was examined by flow cytometry (FIGS. 7 and 8).

The oncolytic activity of recombinant VSVΔ51 encoding the p14 FAST protein (VSV-p14) was compared to a similar construct encoding GFP (VSV-GFP) in cell culture, and in primary and metastatic syngeneic Balb/c tumour models. Compared to VSV-GFP, VSV-p14 increased VSV oncolytic activity in MCF-7 breast cancer spheroids, delayed primary breast cancer tumour growth and prolonged survival in both primary and metastatic breast cancer models, and prolonged survival in a CT26 metastatic colon cancer model (FIGS. 2-6). Survival data and biodistribution results indicate the VSVΔ51 backbone effectively restricted virus replication to the tumor, which was unaffected by p14 (FIG. 4), implying p14 does not compromise the biosafety profile of VSVΔ51.

Figure 10:
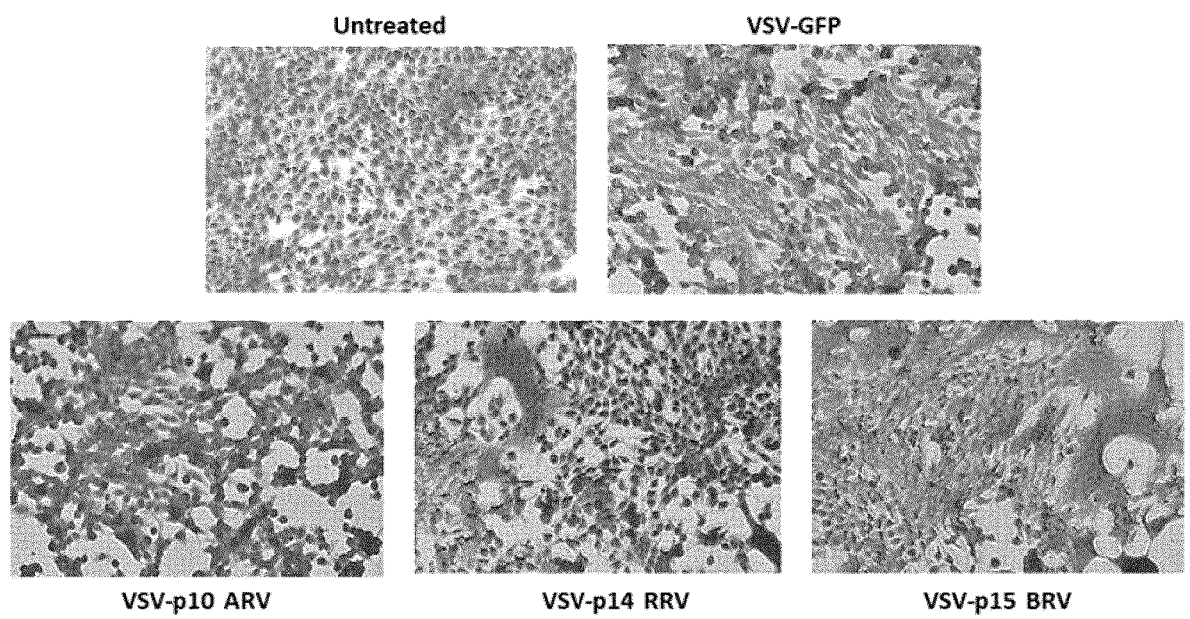
FIG. 10 represents the effects of VSV-GFP or recombinant VSV expressing different FAST proteins (VSV-p14, VSV-p10/ARV, VSV-p10/NBV or VSV-p15) on 4T1 breast cancer cells growing in cell culture. 4T1 cells were mock-infected or infected with the indicated recombinant viruses at a MOI=0.1 and Giemsa-stained at 15 hpi to detect syncytium formation. Different FAST proteins show different abilities to induce cell-cell fusion and syncytium formation; VSV-p15 is hyperfusogenic, VSV-p14 and VSV-p10/NBV are strongly fusogenic, VSV-p10/ARV is weakly fusogenic but cytotoxic.

The effects of VSV-GFP or recombinant VSV expressing different FAST proteins (VSV-p14, VSV-p10/ARV, VSV-p10/NBV or VSV-p15) on 4T1 breast cancer cells growing in cell culture was also tested (FIG. 10). 4T1 cells were mock-infected or infected with the indicated recombinant viruses at a MOI=0.1 and Giemsa-stained at 15 hpi to detect syncytium formation. Different FAST proteins show different abilities to induce cell-cell fusion and syncytium formation; VSV-p15 is hyperfusogenic, VSV-p14 and VSV-p10/NBV are strongly fusogenic, VSV-p10/ARV is weakly fusogenic but cytotoxic.

Figure 11:
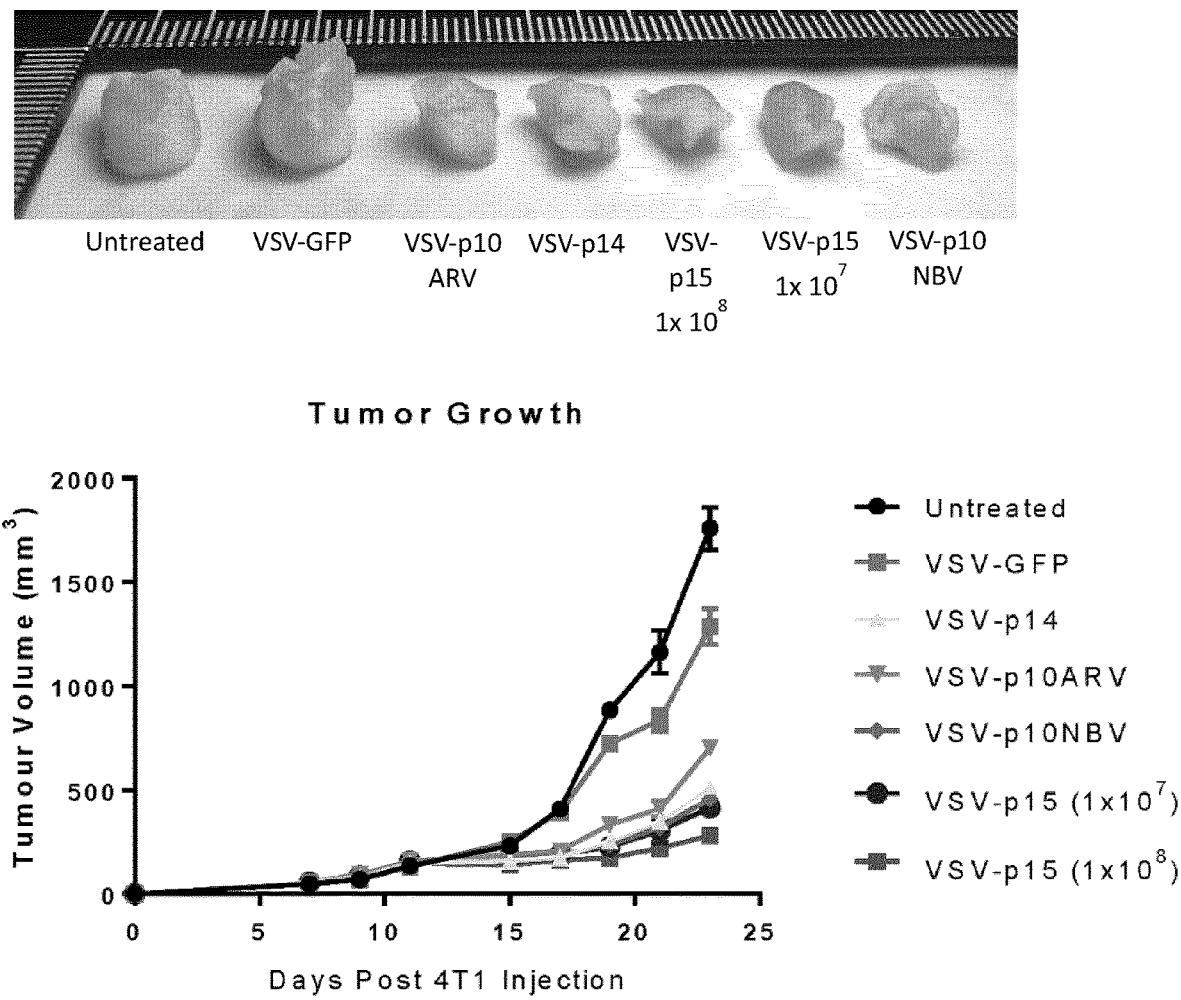
FIG. 11 represents the effects of VSV-GFP or recombinant VSV expressing different FAST proteins (VSV-p14, VSV-p10/ARV, VSV-p10/NBV or VSV-p15) on the growth of primary mammary tumors in BALBc mice. Syngeneic 4T1 subcutaneous mammary tumors were established in BALB/c mice and ten days later animals were mock-treated or treated by one intravenous injection of VSV-GFP or the recombinant VSV expressing different FAST proteins ($1 \times 10^8$ pfu/50 µl injection; a separate treatment group also received VSV-p15 at $1 \times 10^8$ pfu/50 µl injection) followed by four intratumoral injections at the same virus dose on days 11, 12, 13 and 14 (N=5 per treatment group). Top panel: tumors excised at day 15 from a single animal in each treatment group. Bottom panel: tumor size was monitored over time and average tumor volumes±SEM were calculated for each treatment group.

The effects of VSV-GFP or recombinant VSV expressing different FAST proteins (VSV-p14, VSV-p10/ARV, VSV-p10/NBV or VSV-p15) were also evaluated for the growth of primary mammary tumors in BALBc mice (FIG. 11). Syngeneic 4T1 subcutaneous mammary tumors were established in BALB/c mice and ten days later animals were mock-treated or treated by one intravenous injection of VSV-GFP or the recombinant VSV expressing different FAST proteins ($1\times10^8$ pfu/50 µl injection; a separate treatment group also received VSV-p15 at $1\times10^7$ pfu/50 µl injection) followed by four intratumoral injections at the same virus dose on days 11, 12, 13 and 14 (N=5 per treatment group). Top panel: tumors excised at day 15 from a single animal in each treatment group. Bottom panel: tumor size was monitored over time and average tumor volumes±SEM were calculated for each treatment group.

Flow cytometry: All antibodies were purchased from eBioscience or Biolegend (San Diego, CA): purified CD16/32 (clone 97); fluorescein isothiocyanate (FITC)-conjugated CD3 (145-2C11), CD49b (DX5), CD11b (M1/70); phycoerythrin (PE)-labeled CD69 (H1.2F3), CD86 (GL1), Gr-1 (RB6-8C5); peridinin chlorophyll (PERCP)-labeled CD4 (RM4-5), CD11c (H13), TCR-β (H57-597), F4/80 (BM8); allophycocyanin (APC)-labeled CD8α (53-6.7), CD80 (16-10A1). To examine NKT cells by flow cytometry, cells were stained with allophycocyanin-labeled CD1d tetramers loaded with the glycolipid PBS57 (NIH Tetramer Core Facility, Emory Vaccine Center at Yerkes, Atlanta, GA). All cell samples were pre-incubated with anti-CD16/32 antibody to block non-specific binding. Following Fc-receptor blocking, cells were incubated at 4° C. for 20 min with surface-staining antibody panels, washed, and fixed in 2% paraformaldehyde. Data acquisition was performed using a two laser FACSCalibur flow cytometer (BD Biosciences; San Jose, CA) and data analysis was performed using FlowJo (V10.2; FlowJo, LLC; Ashland, OR).

Statistical analyses: Data are expressed as mean±SEM. A non-parametric two-tailed Mann-Whitney U test was used to compare between two groups. Comparisons between more than two groups were made using a Kruskal-Wallis non-parametric ANOVA with Dunn's post-test. Statistical significance was set at $p<0.05$. Survival data was analyzed by log-rank (Mantel-Cox) significance test and the statistical significance level was set using the Bonferroni corrected threshold ($p<(0.05/K)$, where K is the number of comparisons performed. Statistical computations were carried out using GraphPad Instat 3.02 and GraphPad Prism 7.02.

The invention claimed is:

1. A method for treating breast, lung or colon cancer comprising administering to a subject in need thereof a composition consisting of (a) a recombinant oncolytic virus that expresses reovirus fusion-associated small transmembrane (FAST) proteins, wherein the FAST protein is a combination of p14/p15 comprising the ectodomain and transmembrane of p14 and the endodomain of p15; the ectodomain of p14, the transmembrane domain and endodomain of p15; or the ectodomain and endodomain of p14 and the transmembrane of p15, and (b) one or more pharmaceutically acceptable carriers or excipients.

2. The method of claim 1, wherein the breast, lung or colon cancer is a metastatic breast, lung or colon cancer.

3. The method of claim 1, wherein the FAST protein is p14 protein from reptilian reovirus; or a combination of p14 protein from reptilian reovirus and p15 protein from baboon reovirus.

4. The method of claim 3, wherein the oncolytic virus is from herpesvirus, adenovirus, reovirus, measles virus, Newcastle disease virus, vaccina virus and vesicular stomatitis virus.

5. The method of claim 4, wherein the oncolytic virus is vesicular stomatitis virus.

* * * * *